US011786249B2

(12) United States Patent
Smith et al.

(10) Patent No.: US 11,786,249 B2
(45) Date of Patent: *Oct. 17, 2023

(54) APPARATUS AND METHOD FOR DELIVERING SURGICAL TISSUE CONNECTORS INTO AN ABDOMINAL CAVITY AND REMOVING THE SURGICAL TISSUE CONNECTORS FROM THE ABDOMINAL CAVITY

(71) Applicant: Freehold Surgical, LLC, New Hope, PA (US)

(72) Inventors: Jeffrey Smith, Irvine, CA (US); Darren R. Sherman, New Hope, PA (US)

(73) Assignee: Freehold Surgical, LLC, New Hope, PA (US)

( * ) Notice: Subject to any disclaimer, the term of this patent is extended or adjusted under 35 U.S.C. 154(b) by 528 days.

This patent is subject to a terminal disclaimer.

(21) Appl. No.: 16/996,447

(22) Filed: Aug. 18, 2020

(65) Prior Publication Data

US 2020/0375599 A1     Dec. 3, 2020

Related U.S. Application Data

(63) Continuation of application No. 15/860,416, filed on Jan. 2, 2018, now Pat. No. 10,743,878, which is a (Continued)

(51) Int. Cl.
*A61B 17/10*     (2006.01)
*A61B 17/04*     (2006.01)
(Continued)

(52) U.S. Cl.
CPC ...... *A61B 17/105* (2013.01); *A61B 17/00234* (2013.01); *A61B 17/0218* (2013.01);
(Continued)

(58) Field of Classification Search
CPC ............ A61B 17/105; A61B 17/00234; A61B 17/0218; A61B 17/0401; A61B 17/08; A61B 17/10; A61B 17/0469; A61B 2017/00362; A61B 2017/0409; A61B 2017/0411; A61B 2017/0414;
(Continued)

(56) References Cited

U.S. PATENT DOCUMENTS

| 2006/0106423 | A1* | 5/2006 | Weisel ............... A61B 17/0401 606/232 |
| 2010/0292732 | A1* | 11/2010 | Hirotsuka ............... B29C 45/00 606/232 |
| 2012/0116153 | A1* | 5/2012 | Scott ................ A61B 17/06109 600/37 |

* cited by examiner

*Primary Examiner* — Tan-Uyen T Ho
*Assistant Examiner* — Rachel S Highland
(74) *Attorney, Agent, or Firm* — Crockett & Crockett, PC; K. David Crockett, Esq.

(57) ABSTRACT

An apparatus and its method of use in delivering surgical tissue connectors into an area of the body and removing the surgical tissue connectors from the body area. The tissue connectors are connected to a base which allows for easy adjustment of the tissue connectors along a cord. The base includes a locking mechanism which impinges a sliding knot in the cord, and, in alternate configurations of the locking mechanism and knot, impinges on the sliding knot to prevent sliding in a loosening direction but allow sliding in a tightening direction, or allows sliding in a loosening direction.

8 Claims, 10 Drawing Sheets

Related U.S. Application Data continuation of application No. 14/411,243, filed as application No. PCT/US2013/047862 on Jun. 26, 2013, now Pat. No. 9,855,044.

(60) Provisional application No. 61/666,380, filed on Jun. 29, 2012.

(51) Int. Cl.
*A61B 17/02* (2006.01)
*A61B 17/00* (2006.01)
*A61B 17/08* (2006.01)

(52) U.S. Cl.
CPC .......... *A61B 17/0401* (2013.01); *A61B 17/08* (2013.01); *A61B 17/10* (2013.01); *A61B 17/0469* (2013.01); *A61B 2017/00362* (2013.01); *A61B 2017/048* (2013.01); *A61B 2017/0409* (2013.01); *A61B 2017/0411* (2013.01); *A61B 2017/0414* (2013.01); *A61B 2017/0446* (2013.01); *A61B 2017/0464* (2013.01); *A61B 2017/0496* (2013.01)

(58) Field of Classification Search
CPC .... A61B 2017/0446; A61B 2017/0464; A61B 2017/048; A61B 2017/0496
See application file for complete search history.

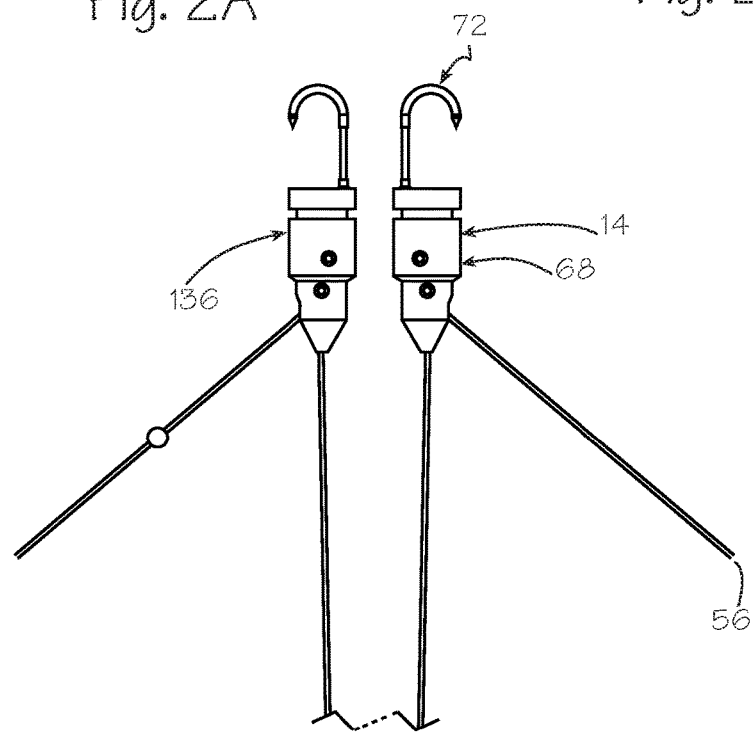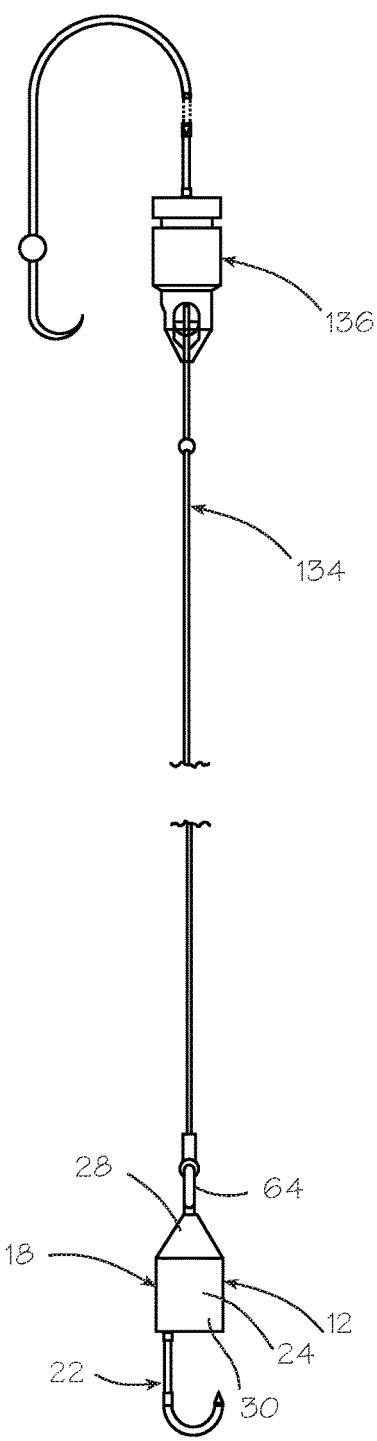

APPARATUS AND METHOD FOR DELIVERING SURGICAL TISSUE CONNECTORS INTO AN ABDOMINAL CAVITY AND REMOVING THE SURGICAL TISSUE CONNECTORS FROM THE ABDOMINAL CAVITY

This application is a continuation of U.S. application Ser. No. 15/860,416, filed Jan. 2, 2018, which is a continuation of U.S. application Ser. No. 14/411,243, filed Dec. 24, 2014, now U.S. Pat. No. 9,855,044, which is a national stage of International Application PCT/US2013/047862 filed Jun. 26, 2013, which claims priority to U.S. Provisional Application 61/666,380 filed Jun. 29, 2012.

FIELD OF THE INVENTIONS

The present invention is directed to an apparatus and its method of use in delivering surgical tissue connectors into an area of the body and removing the surgical tissue connectors from the body area. More specifically, the present invention is directed to a surgical tissue connector apparatus having at least two tissue connectors connected by a length of cord and a delivery and removal tube. At least one of the tissue connectors has a base with a tapered, beveled or chamfered surface projecting from one end of the base. A hook or other type of tissue connector projects from the opposite side of the base. The hook is positioned on the base where a peripheral side surface of the base shields the hook from unintentionally snagging objects. The base peripheral surface is also dimensioned to slide easily through an interior bore of the tube. This enables the base and the projecting hook to be easily delivered through the tube into an area of the body. The chamfered or tapered surface on the base is positioned to engage with the distal end opening of the tube and direct the base into the center of the tube as the surgical tissue connector is retracted into the tube from the body area in removing the apparatus from the abdominal cavity.

DESCRIPTION OF THE RELATED ART

In laparoscopic surgery procedures, it is often necessary to pass surgical tissue connectors though a cannula, trocar, endoscope or other similar device that is positioned through an incision in the body to deliver the tissue connectors into an area of the body where the connectors are used in a laparoscopic surgery procedure. A disadvantage associated with the current constructions of surgical tissue connectors and the tubular delivery device used to deliver the connectors into the body and then remove the connectors from the body is that often the connectors will snag or catch a portion of the tubular delivery device being used to deliver or retrieve the connectors.

SUMMARY OF THE INVENTION

The present invention overcomes the above described disadvantages associated with tissue connectors used in laparoscopic and other surgery procedures by providing an apparatus that facilitates the delivery of a surgical tissue connector through a tubular delivery device and into the body, and the subsequent removal of the surgical tissue connector through the tubular device from the body.

The basic construction of the apparatus of the invention includes at least two surgical tissue connectors. Each tissue connector has a base. The base has a side surface that extends around the base, and a distal end surface and proximal end surface at the opposite ends of the side surface. In one embodiment of the tissue connector, the base side surface is a cylindrical surface having a center axis that defines mutually perpendicular axial and radial directions relative to the base.

A hook is secured stationary to and projects axially from the base distal end surface. The hook has a shank portion that extends axially from the base distal end surface. The shank portion is substantially parallel with the base center axis but spaced radially from the center axis. The hook also has a bent portion that extends from the shank portion across the base distal end surface and through the center axis to a distal end tip of the hook. The end tip and the shank are radially spaced on opposite sides of the base center axis and the end tip does not project radially beyond the base side surface. Thereby, the base side surface shields the end tip of the hook from snagging or catching with other objects.

The base proximal end surface of at least one of the connectors has a chamfered or tapered configuration that tapers as the proximal end surface extends axially away from the base side surface. In one embodiment of the apparatus, the base proximal end surface has a conical configuration. The conical configuration of the base proximal end surface extends axially from the base side surface to an apex that is centered on the base distal end surface.

The apparatus also includes a length of cord that extends between the proximal end surfaces of the tissue connectors. In one embodiment of the apparatus, the length of the cord extending between the tissue connectors is flexible and can be adjusted.

The apparatus also includes a tissue connector delivery and removal tube. In one embodiment of the apparatus, the tube has a straight length with opposite proximal and distal ends, and a cylindrical interior bore that extends through the length of the tube. The interior bore has an interior diameter dimension that is slightly larger than an exterior diameter dimension of the base cylindrical side surface. This enables the tissue connectors to easily slide through the interior bore of the tube then delivering the tissue connectors through the tube, or removing the tissue connector through the tube. Additionally, the tapered configuration of the base proximal end surface of at least one of the tissue connectors enables that tissue connector to be easily pulled into the tube at the tube distal end. Removing the apparatus by pulling the other tissue connector through the tube distal end and then pulling the cord and the tapered tissue connector into the tube causes the tapered configuration of the base proximal end surface to first enter the end of the tube, whereby the tapered configuration centers the base cylindrical side surface relative to the tube interior bore as the tapered proximal end surface is pulled into the tube interior bore. With the base side surface centered in the tube interior bore, the hook projecting from the base distal end surface is prevented from snagging or catching the distal end of the tube as the tissue connector is pulled into and through the tube.

The apparatus also includes a rod having a straight length that is dimensioned to be inserted into the tube proximal end to push the tissue connectors and their connecting cord through the tube interior bore to deliver the tissue connectors and the connecting cord from the tube distal end.

When use of the apparatus in the surgical procedure is complete, the apparatus can be easily removed from the body by inserting the tube through a cannula or an incision to position the tube distal end adjacent the connectors and the cord, and then inserting a surgical grasper through the tube and grasping the tissue connector without the tapered end surface. The tissue connector is grasped at its hook. Retracting the grasper back through the tube will move the grasped connector into the tube and then pull the cord into the tube interior bore. As the cord is pulled through the tube bore it pulls the tapered proximal end surfaces of the other tissue connectors into the bore. The tapered proximal end surface of the connector will center the connector and the cylindrical side surface of the connector relative to the interior bore as the connector enters the tube distal end and passes through the interior bore. The cylindrical side surface of the connector prevents the hook extending from the distal end surface of the connector from snagging or catching against the tube distal end as the connector enters into and passes through the tube interior bore.

As described above, the apparatus of the invention and its method of use facilitate the delivery of surgical tissue connectors to a surgery site and facilitate the removal of the surgical tissue connectors from the surgery site.

DESCRIPTION OF THE DRAWINGS

Further features of the apparatus of the invention and its method of use are set forth in the following detailed description of the apparatus and method and are shown in the drawing figures.

FIGS. 2a and 2b show further embodiments of the apparatus similar to that of FIGS. 1a and 1b.

DETAILED DESCRIPTION OF THE PREFERRED EMBODIMENTS

Figure 1A:
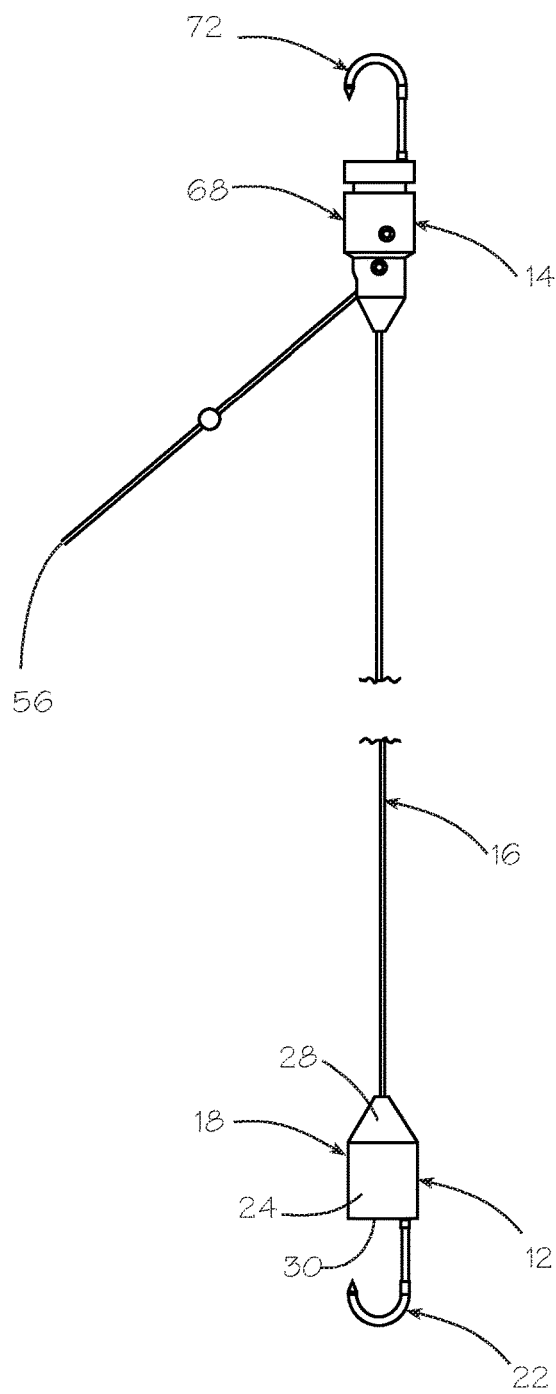
FIGS. 1a and 1b show an embodiment of the apparatus comprising a pair of tissue connectors connected by a cord where one of the tissue connectors employs a releasable one-way cord lock that enables adjusting the length of the portion of the cord extending between the pair of tissue connectors.
Figure 1B:
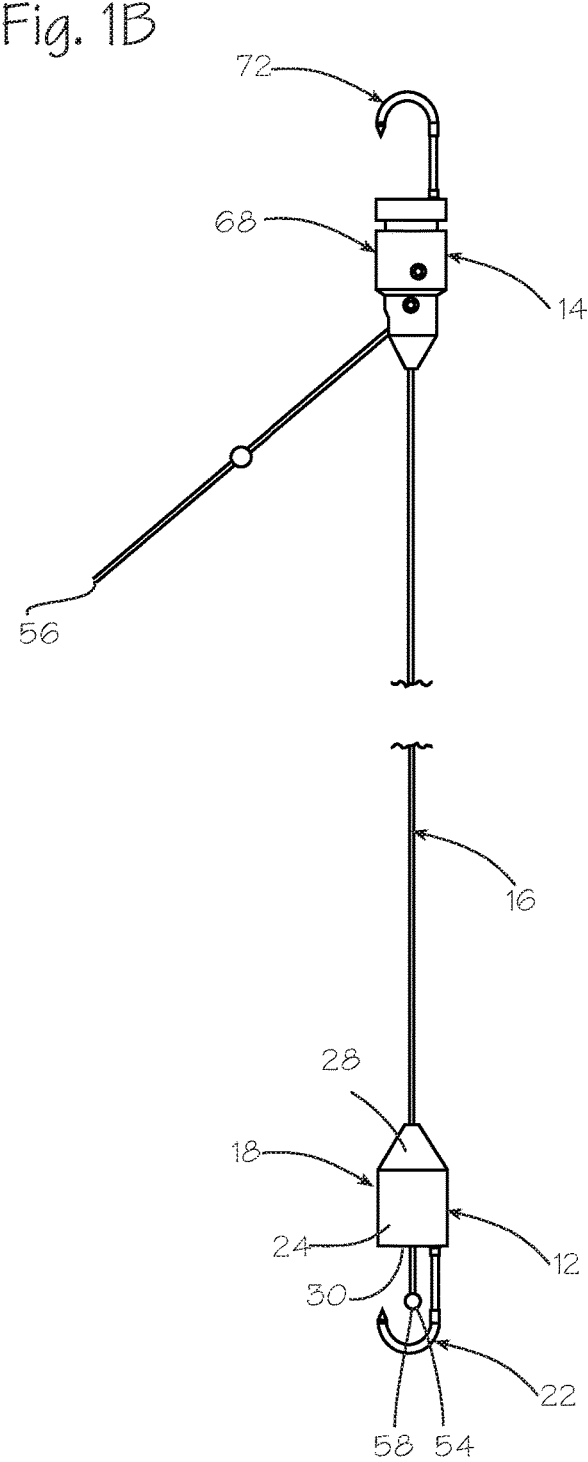
Figure 3:
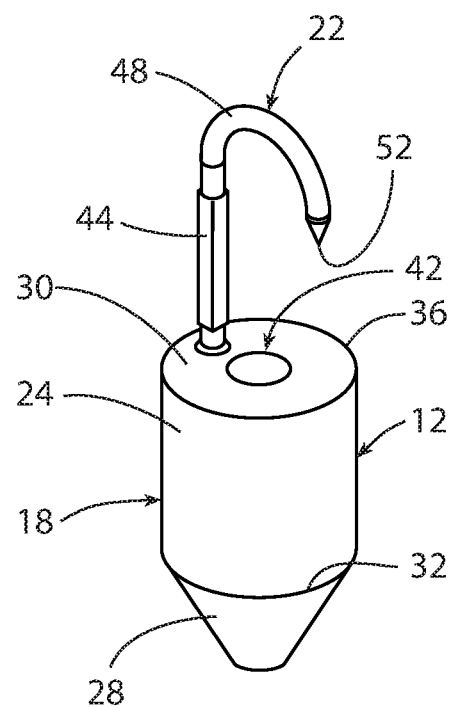
FIG. 3 is a perspective view of one of the tissue connectors.
Figure 4:
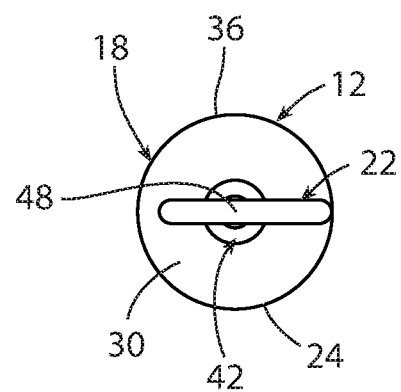
FIG. 4 is a plan view of the tissue connector of FIG. 3.
Figure 5A:
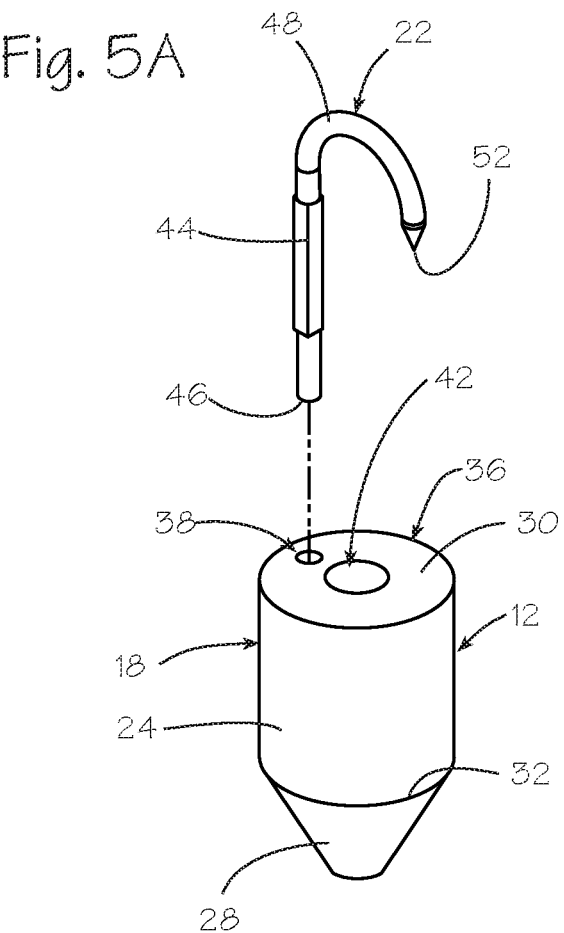
FIGS. 5a and 5b illustrate the assembly of the tissue connector of FIG. 3.
Figure 5B:
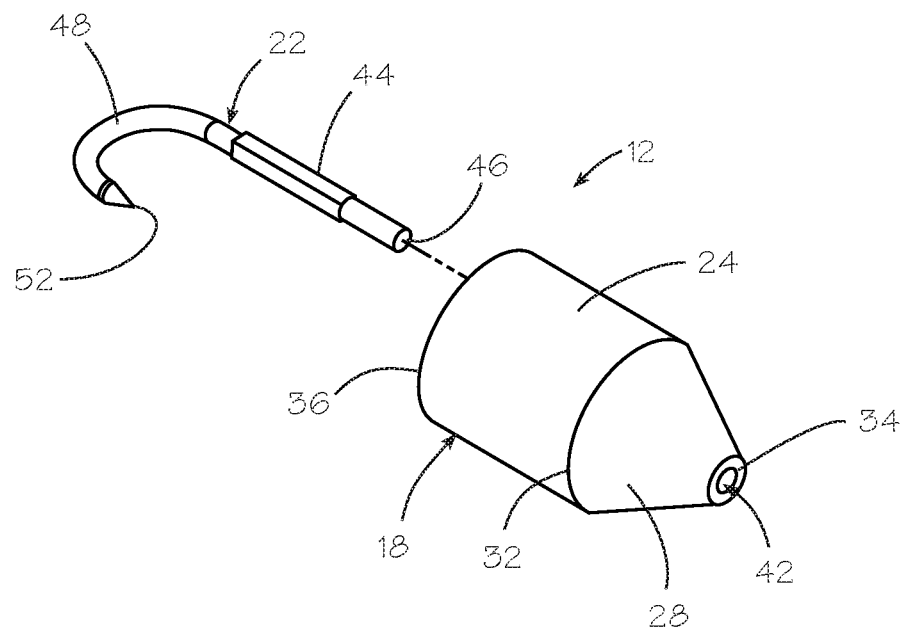
Figure 6:
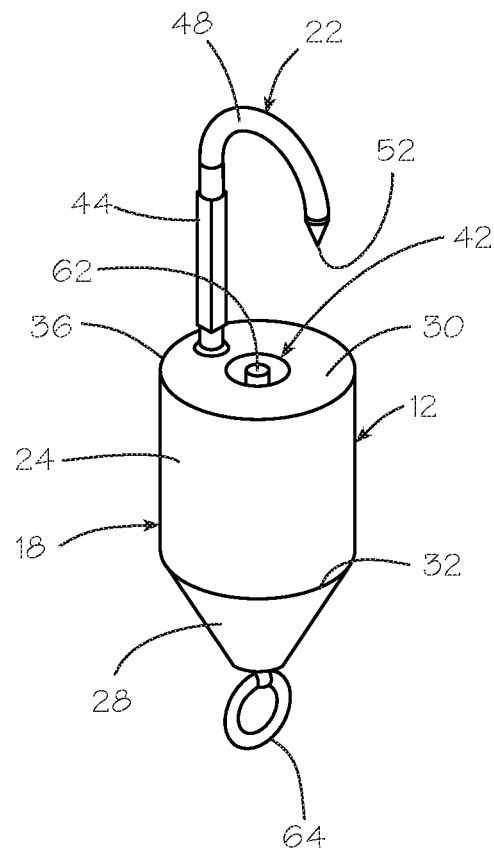
FIG. 6 is a perspective view of a further embodiment of a tissue connector.
Figure 7:
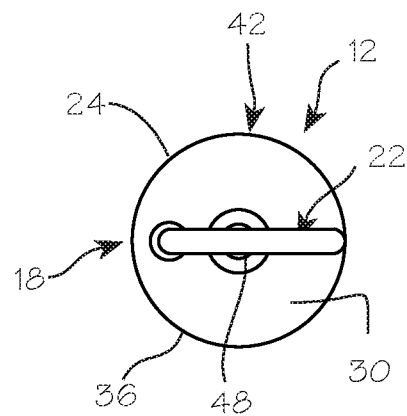
FIG. 7 is a plan view of the tissue connector of FIG. 6.
Figure 8A:
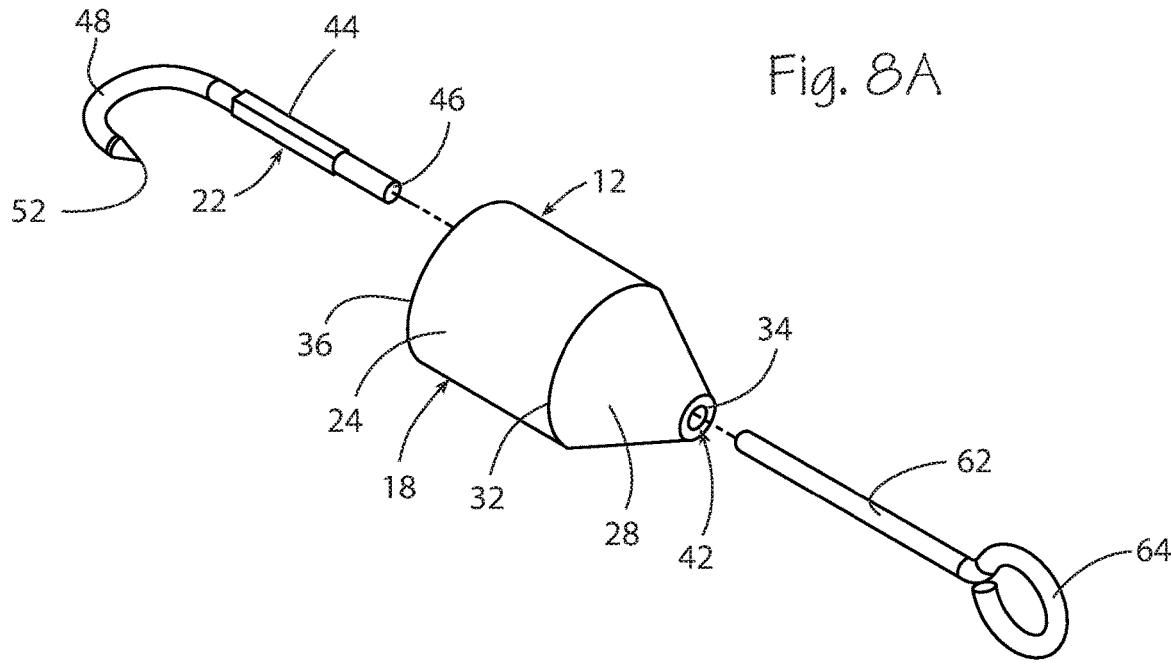
FIGS. 8a and 8b illustrate the assembly of the tissue connector of FIG. 6.
Figure 8B:
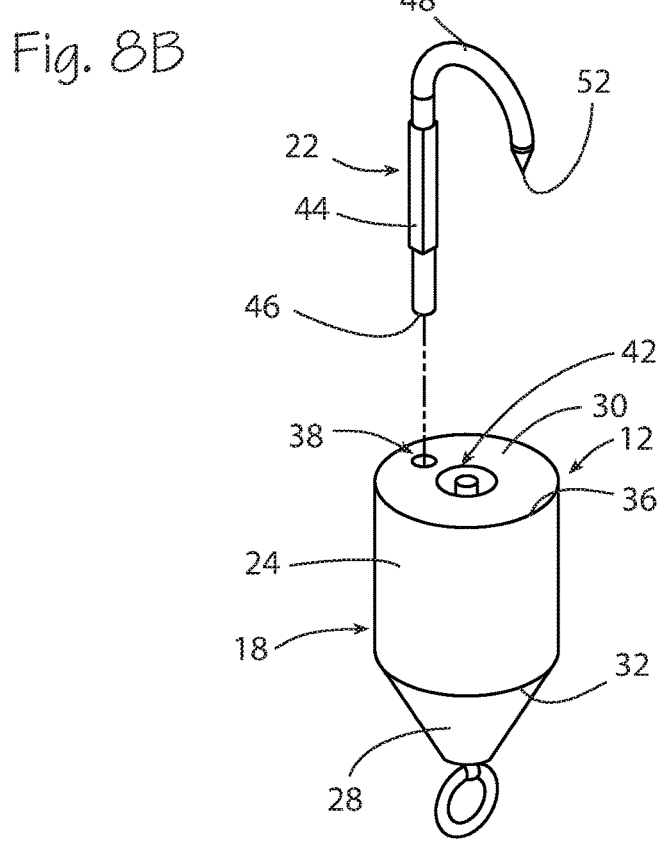
Figure 9:
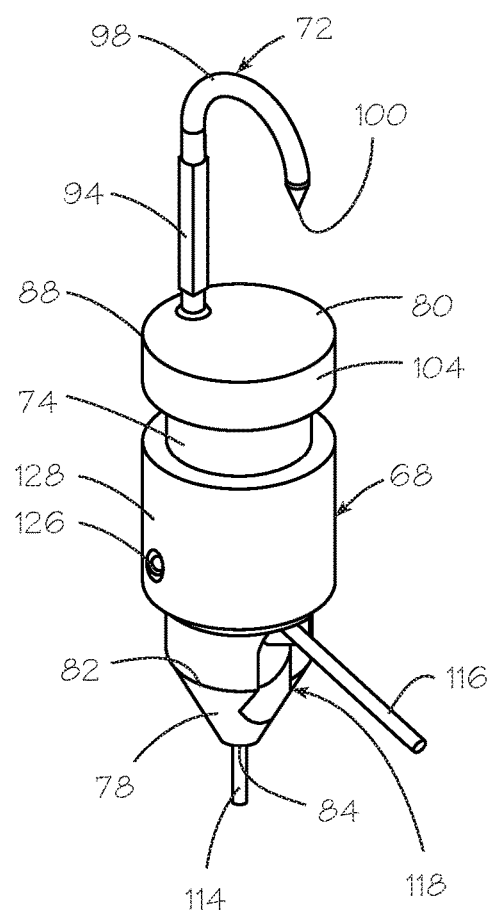
FIG. 9 is a perspective view of a further embodiment of a tissue connector.
Figure 10:
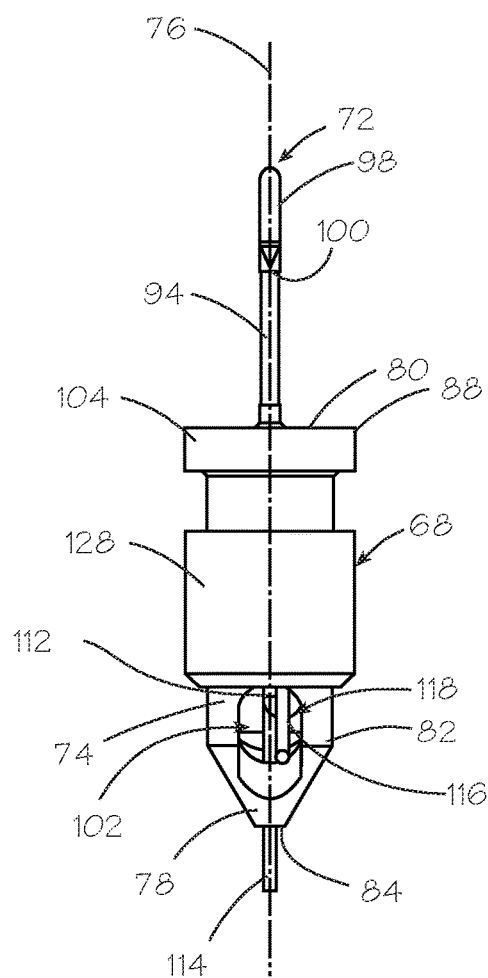
FIG. 10 is a side view of the tissue connector of FIG. 9.
Figure 12:
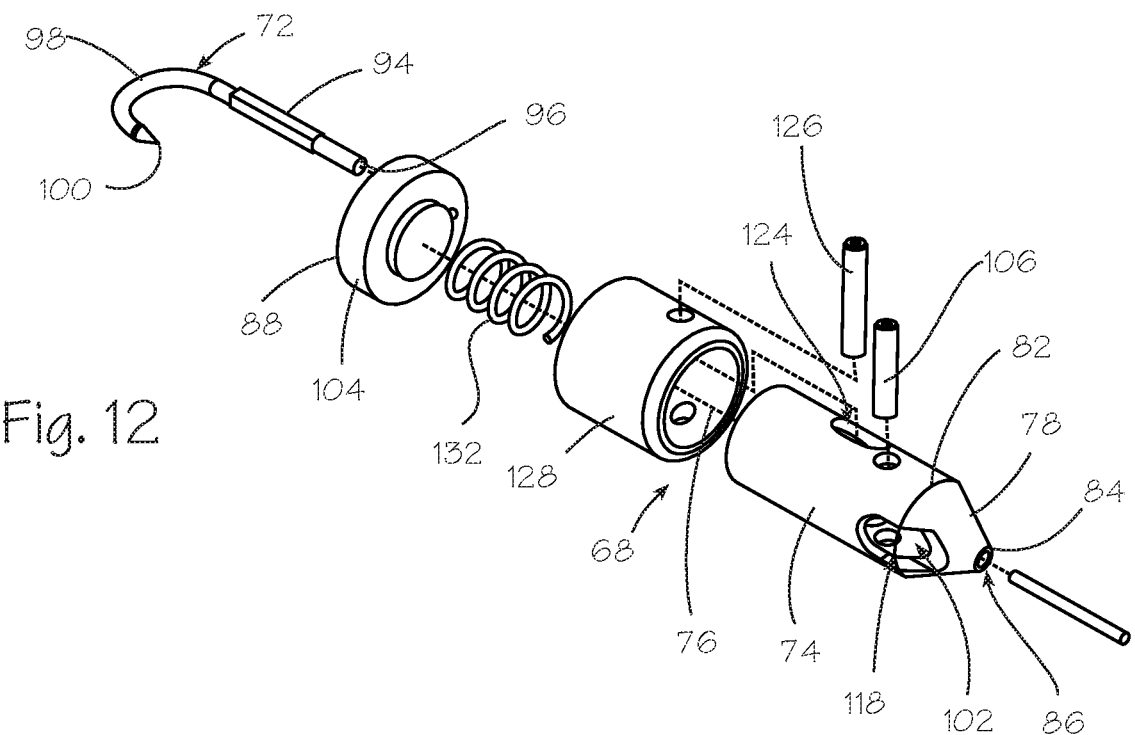
FIG. 12 is a perspective view of the disassembled component parts of the tissue connector of FIG. 9.

FIGS. 1A and 1B show an embodiment of the tissue connector apparatus of the invention that is constructed to facilitate the delivery of the tissue connectors through a cannula or other type of tubular delivery device to a surgical site of a body for use in a laparoscopic surgery or other type of surgical procedure, and facilitate the removal of the tissue connectors of the apparatus following completion of the procedure. As is conventional with laparoscopic apparatus, the component parts of the apparatus are dimensioned to be inserted through an incision or through a cannula, trocar, endoscope or other type of tubular delivery device extending into the body to position the apparatus at a surgery site. All of the component parts of the apparatus to be described are constructed of biocompatible materials.

The first embodiment of the apparatus is shown in FIGS. 1a and 1b. The embodiment shown is basically comprised of a first tissue connector 12, a second tissue connector 14 and a length of cord 16 extending between and connecting the two tissue connectors. The cord could be a suture, IV tubing or other equivalent types of cord and could be one piece or several pieces connected together.

Details of the construction of the first tissue connector 12 are shown in FIGS. 3, 4, 5a and 5b. The first tissue connector 12 is comprised of a base 18 and a hook 22. The base 18 for the most part is a solid single piece of material having a side exterior surface that extends completely around the base. In the embodiment shown in the drawing figures, the side surface 24 is cylindrical. The cylindrical surface 24 has a center axis 26 that defines mutually perpendicular axial and radial directions relative to the base. The base also has a proximal end surface 28 at one axial end of the base and a distal end surface 30 at an opposite axial end of the base.

The proximal end surface 28 is chamfered or tapers as it extends axially away from the base side surface 24. In the embodiment shown, the proximal end surface 28 has a conical configuration with a circular peripheral edge 32 defined by the intersection of the proximal end surface with the cylindrical base side surface 24. The proximal end surface 28 tapers as it extends axially from the base side surface 24 to an apex end 34 of the proximal end surface.

The base distal end surface 30 is substantially flat. The distal end surface 30 has a circular peripheral edge 36 defined by the intersection of the distal end surface with the cylindrical base side surface 24.

A hook hole 38 is formed in the base distal end surface 30. The hook hole 38 is spaced radially inwardly from the distal end surface peripheral edge 36 and radially from the center axis 26. The hook hole extends axially into the base a short distance from the distal end surface 30 and does not extend entirely through the base. A center hole 42 is also formed in the base at the center of the base distal end surface 30. The center hole 42 extends axially through the base and emerges at the apex 34 of the base proximal end surface 28. The center hole 42 has a slightly larger interior diameter dimension adjacent the base distal end surface 30 than the interior diameter dimension of the hole 42 adjacent the apex 34 of the base proximal end surface 28.

The hook 22 has a straight shank portion 44 extending from a proximal end 46 of the hook. The hook shank portion adjacent the hook proximal end 46 is dimensioned with a cylindrical exterior surface that fits tightly into the hook hole 38 in the base distal end surface 30. The hook shank portion 34 is secured stationary to the base by laser welding or other equivalent means. The hook 22 is secured to the base distal end surface 32 with the hook shank portion 34 extending axially from the distal end surface 32 substantially parallel with the center axis 26, but radially spaced from the center axis. The hook shank portion 44 extending from the distal end surface 30 has a square or other similar cross-section configuration to facilitate grasping the hook with a surgical grasper and preventing the hook shank from rotating in the grasper. The shank portion 44 extends axially from the base distal end surface 30 to a bent portion 48 of the hook that extends radially across the distal end surface 30, through the base center axis 26 and to a distal end tip 52 of the hook. The distal end tip 52 and shank portion 44 of the hook are each radially spaced on opposite sides of the base center axis. The shank portion 44 and end tip 52 are both spaced a radial distance dimension on opposite sides of the center axis 26 that is smaller than the base radius dimension, whereby the hook bent portion and tip do not project radially beyond the cylindrical side surface of the base. Although the hook 22 is shown as the part of the tissue connector 12 that is removably attachable to body tissue, other equivalent devices that do not project radially beyond the side surface of the base could be used.

In the embodiment of the apparatus shown in FIGS. 1a and 1b, the cord 16 has a flexible length with opposite first 54 and second 56 ends. The cord first end 54 passes through the center hole 42 of the first tissue connector 12 from the proximal end surface 28 to the distal end surface 30. A knot 58 is tied in the cord first end 54. A medical grade glue, for example cyanoacrylate is applied to the knot. The cord is pulled from the base proximal end surface 28 to pull the knot 58 into the center hole 42 in the base distal end surface 30. The knot 56 is too large to pass though the smaller portion of the center hole 42 that emerges from the apex 34 of the proximal end surface 28. Thereby, the cord first end 54 is secured to the first tissue connector 12 with the cord extending from the base proximal end surface 28 of the tissue connector.

FIGS. 6, 7, 8a and 8b show an alternate embodiment of the first tissue connector where a post 62 of an eyelet ring 64 is inserted through the base center hole 42 from the base proximal end surface 28. The post 62 is secured to the base by laser welding the end of the post 62 in the center hole at the base distal end surface 32. The eyelet ring 64 could be secured to the base by other equivalent means. The first end 54 of the cord 16 is then secured to the eyelet 64 by a knot being tied in the cord around the eyelet ring 64 and the knot being secured by a medical grade glue.

Details of the construction of the second tissue connector 14 are shown in FIGS. 9, 10, 11 and 12.

The second tissue connector 14 is also basically comprised of a base 68 and a hook 72 projecting from the base. The base 68 has a side surface 74 that extends completely around the base. The in embodiment shown in the drawing figures the side surface 74 is cylindrical and has a center axis 76 that defines mutually perpendicular axial and radial directions relative to the base 68. The base 68 also has a proximal end surface 78 at one axial end of the base and a distal end surface 80 at the opposite axial end of the base.

The base proximal end surface 78 is chamfered or tapers as it extends axially away from the cylindrical side surface 74. In the embodiment of the second tissue connector 68 shown, the base proximal end surface 78 has a conical configuration with a circular peripheral edge 82 defined by the intersection of the proximal end surface 78 with the cylindrical base side surface 74. The proximal end surface 78 tapers as it extends from the cylindrical side surface 74 to an apex 84 on the proximal end surface. A hole 86 passes through the center of the apex 84 of the proximal end surface 78 to an interior bore of the base that is described later.

The base distal end surface 80 is substantially flat. The distal end surface 80 has a circular peripheral edge 88 defined by the intersection of the distal end surface 80 and the cylindrical base side surface 74.

A hook hole 92 is formed in the base distal end surface 80. The hook hole 92 is spaced radially inwardly from the distal end surface peripheral edge 88 and radially from the center axis 76. The hook hole 92 extends axially into the base a short distance from the distal end surface 80 and does not extend entirely through the base.

The hook 72 of the second tissue connector 14 has substantially the same construction as the hook 22 of the first tissue connector 12. The hook 72 has a straight shank portion 94 extending from a proximal end 96 of the hook. Adjacent the proximal end 96 the hook shank portion has a cylindrical configuration dimensioned to fit tightly into the hook hole 88 on the distal end surface 80. The hook shank portion 94 is secured to the base distal end surface 80 by laser welding or other equivalent means. The hook shank portion 94 extends axially from the base distal end surface 80 substantially parallel with the base center axis 76 but spaced radially from the center axis. The shank portion 94 extending from the distal end surface 80 has a square or other similar cross-section configuration that facilitates grasping the shank portion with surgical graspers and preventing rotation of the shank portion in the graspers. The hook shank portion 94 extends axially from the base to a bent portion 98 of the hook that extends radially over the base distal end surface 80 and through the base center axis 76. The hook bent portion 98 extends from the shank portion 94 to a distal end tip 100 of the hook. The hook distal end tip 100 and shank portion 94 are both spaced a radial distance dimension on opposite sides of the center axis 76 that is smaller than the base radius dimension, whereby the hook bent portion and the distal end tip 100 do not project radially beyond the cylindrical side surface 74 of the base. Although the hook 72 is shown as the part of the tissue connector that is removably attachable to body tissue, other equivalent devices that do not project radially beyond the side surface of the base could be used. Additionally, although both tissue connectors 12, 14 are described as having chamfered or tapered surfaces 28, 78, it is not necessary that both have tapered surfaces for the intended functioning of the apparatus.

Although the first 12 and second 14 tissue connectors have similar constructions as discussed above, the second tissue connector 14 is constructed with a releasable one-way cord lock that enables the length of the portion of the cord 16 extending between the two tissue connectors 12, 14 to be adjusted.

The second tissue connector base 68 has a tubular configuration with a cylindrical housing wall having the base cylindrical side surface 74 on its exterior, and a hollow interior bore 102 extending through the length of the housing wall interior.

A disk-shaped cap 104 is secured to a distal end of the base housing wall by laser welding or other equivalent means. The disk-shaped cap 104 defines the distal and surface 80 of the base.

A rod or pin 106 is secured to the base 68 in the base interior bore 102. The rod 106 extends radially across the base interior bore 102 adjacent the proximal end surface 78 of the base. Opposite ends of the rod 106 are secured to the interior surface of the base cylindrical housing.

The cord 6 is secured to the second tissue connector 14 inside the base interior bore 102. The second end 56 of the cord 16 extends through the center hole 86 in the apex of the base proximal end surface 78 and into the hollow interior bore 102 of the base. An intermediate portion of the cord 112 is wrapped around the rod 106 in the base interior, thereby attaching the cord 16 to the second tissue connector 14. The intermediate portion of the cord 112 is wrapped around the rod 106 by being tied in a knot around the rod. The preferred knot 112 is a Munter hitch knot. A first portion 114 of the cord length extends from the intermediate portion 112 though the base center hole 86. The cord first portion 114 extends from the proximal end surface 78 of the base to the cord first end 54 attached to the first tissue connector 12. A second portion of the cord length 116 extends from the cord intermediate portion 112 through a side hole 118 in the base cylindrical side surface 74 and the proximal end surface 78. The side hole 118 is provided to separate the cord first portion 114 and the cord second portion 116 to prevent tangling. The side hole 118 also allows for a greater angle that the cord second portion 116 can be pulled from the connector. The second portion of the cord 116 extends from second tissue connector 14 to a second, free end 122 of a cord.

The releasable one-way cord lock is comprised of a pair of slots 124 that are formed in radially opposite sides of the cylindrical side wall of the base 68. As seen in the drawing figures, the slots 124 extend axially along a portion of the cylindrical wall of the base 68 and are positioned radially to one side of the base center axis 76. A lock pin 126 is positioned in the slots 124 and extends from one slot 124 across the interior bore of the base 68 to the other slot. The lock pin 126 slides axially along the slots 124.

Figure 11:
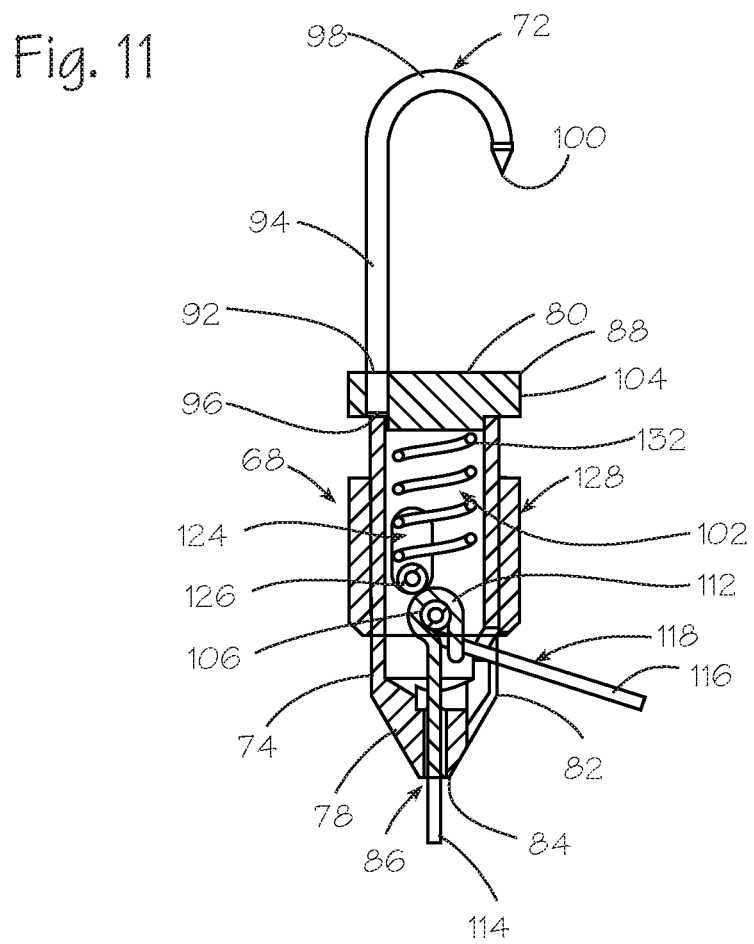
FIG. 11 is cross-section view of the tissue connector of FIG. 9.

An actuator 128 is mounted on the base cylindrical side surface 74 and is connected to the lock pin 126 inside the base. The actuator 128 is formed as cylindrical sleeve that surrounds the base cylindrical side surface 74. The actuator 128 is mounted on the cylindrical side surface 74 of the base 68 for axially reciprocating movements between first and second positions of the actuator 128 relative to the base 68. The opposite ends of the lock pin 126 project beyond the slots 124 in the base cylindrical side surface 74 and are secured in opposite sides of the actuator 128. Moving the actuator 128 to its first position shown in FIG. 11 causes the lock pin 126 to engage against the cord intermediate portion 112 that is wrapped around the rod 106. In FIG. 11, the pin 126 prevents the knot 112 from rotating counterclockwise around the rod 106 when the knot 112 is in a 3 o'clock position, or to the right of the rod as shown in FIG. 11 and the cord first portion 114 is pulled. The engagement of the lock pin 126 against the cord intermediate portion or knot 112 locks the cord and prevents the first portion of the cord length 114 from being pulled from the proximal end surface 78 of the second tissue connector 14. However, in the position of the knot 112 shown in FIG. 11 the cord second portion 116 can be pulled from the second tissue connector 14 to shorten the length of the cord first portion 114, but the cord first portion 114 cannot be pulled from the connector. Moving the actuator 128 to its second position causes the lock pin 126 to disengage from the cord intermediate portion or knot 112. With the pin 126 moved upward, the cord first portion 114 can be pulled to move the knot 112 counterclockwise from the 3 o'clock position to a 6 o'clock position as viewed in FIG. 11. This allows the length of the cord first portion 114 extending between the second tissue connector 14 and the first tissue connector 12 to be pulled from the second tissue connector 14 to adjust or increase the length of the cord first portion 114. With the pin 126 moved upward the cord second portion 116 can also be pulled from the connector.

A biasing device 132 urges the lock pin 126 to its first position shown in FIG. 11. In the drawing figures the biasing device 132 is coiled spring. Other equivalent types of biasing devices could be employed.

The slot 124 and the pin 126 are off center relative to the base cylindrical side surface 74 to facilitate the knot 112 pushing the pin 126 upward against the bias of the spring 132 when the cord second portion 116 is pulled and the knot 112 moves clockwise from the 6 o'clock position to the 3 o'clock position relative to the rod 106.

Tissue connectors having one way cord locks such as that described above are disclosed in the currently pending international patent application No. PCT/US2011/01494 which is assigned to the assignee of this invention and is incorporated herein by reference.

FIG. 2a shows a further embodiment of the apparatus of the invention comprising the first tissue connector 12 and the second tissue connector 14 connected by the length of cord 16. However, the first end of the length of cord 16 is connected to the first tissue connector 12 having the eyelet ring 64 that was described earlier. In addition, a second length of cord 134 connects a third tissue connector 136 to the first tissue connector 12. The construction of the third tissue connector 136 is substantially the same as that of the second tissue connector 14 described earlier. In the embodiment of FIG. 2A, at least two of the three tissue connectors would require tapered proximal end surfaces in order for the apparatus to function as intending in removing the apparatus from a surgical site as described below.

FIG. 2B shows a still further embodiment of the apparatus where the tissue connector hook 72 or other equivalent device is not directly connected to the base 68 of the second tissue connector 14, but is connected by a further length of suture 138.

Figure 13:
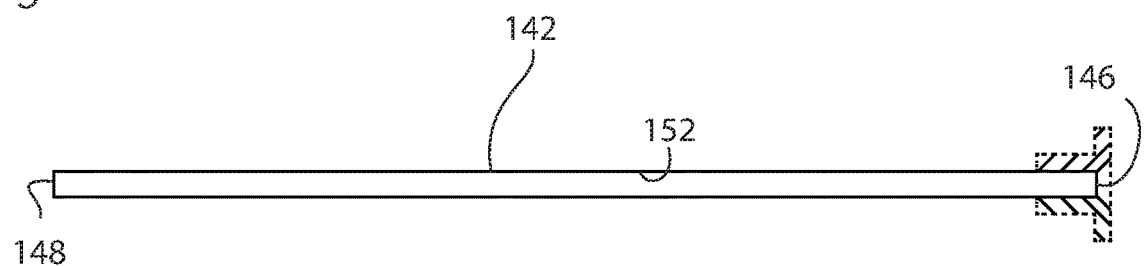
FIG. 13 is a cross-section view of the delivery and removal tube of the apparatus.
Figure 14:
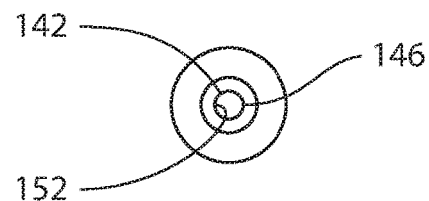
FIG. 14 is an end view of the proximal end of the delivery and removal tube.
Figure 15:
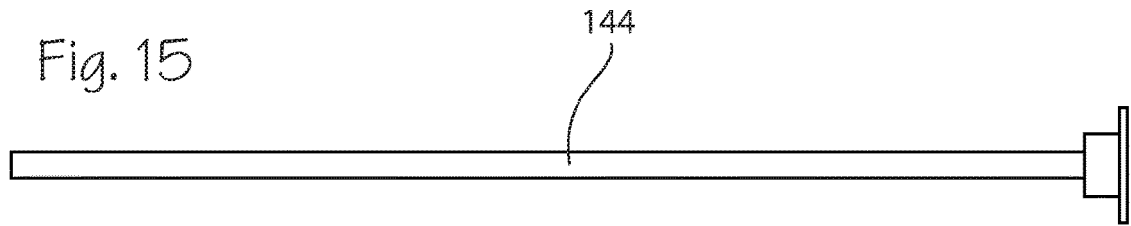
FIG. 15 is a side view of the delivery rod of the apparatus.
Figure 16:
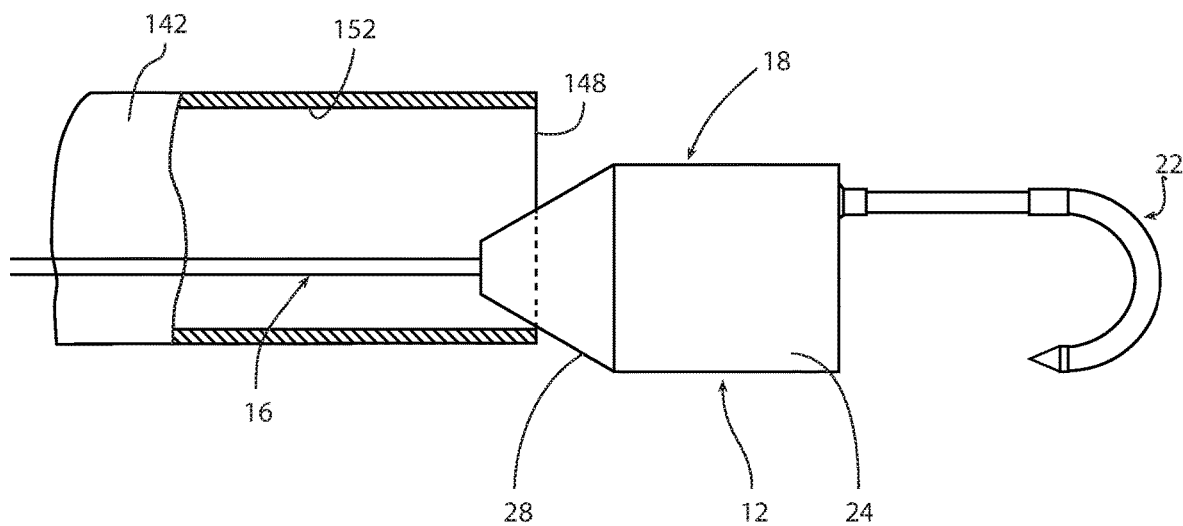
FIG. 16 is a partial sectioned view of the apparatus illustrating the method of removing a tissue connector of the apparatus from an abdominal cavity using the delivery and removal tube of the apparatus.
Figure 17:
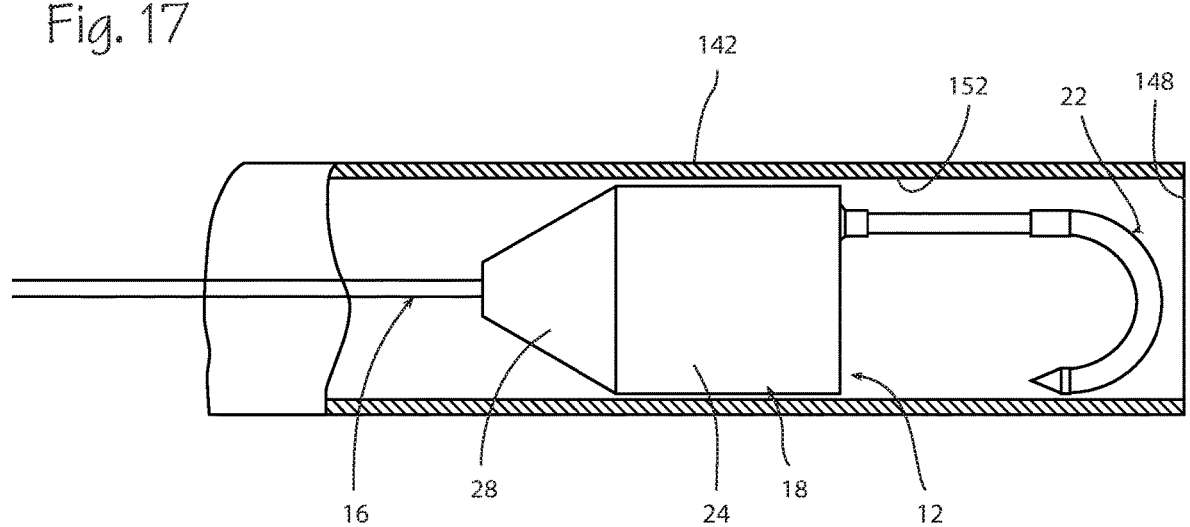
FIG. 17 is a partial sectioned view of the apparatus further illustrating the method of removing a tissue connector of the apparatus from an abdominal cavity using the delivery and removal tube of the apparatus.

The apparatus of the invention also comprises a tissue connector deliver and removal tube 142 shown in FIGS. 13 and 14, and a delivery rod 144 shown in FIG. 15.

In one embodiment of the apparatus, the tube 142 has a straight length with opposite proximal 146 and distal 148 ends. An interior bore having a smooth cylindrical interior surface 152 extends through the length of the tube. The cylindrical interior surface 152 has an interior diameter dimension that is just slightly larger than the exterior diameter dimension of the first tissue connector base cylindrical side surface 24 and the second tissue connector base cylindrical side surface 74. This enables the tissue connectors 12, 14 to easily slide through the interior bore of the tube when delivering the tissue connectors through the tube, or removing the tissue connectors through the tube.

The delivery rod 144 has a straight length that is dimensioned to be inserted into the tube proximal end 146 to push the tissue connectors 12, 14 and the connecting cord 16 through the tube interior bore to deliver the tissue connectors and the connecting cord from the tube distal end 142 and to a surgical site in a body.

Additionally, the tapered configuration of the base proximal end surface 28 of the first tissue connector 12 and the tapered configuration of the base proximal end surface 78 of the second tissue connector 14 enables the tissue connectors to be easily pulled into the interior bore of the tube 42 at the tube distal end 148. However, it is only necessary that one tissue connector 12 have a tapered proximal end surface in a two-connector embodiment of the apparatus such as that shown in FIGS. 1A and 1B. When it is desired to remove the tissue connectors 12, 14 from a surgical site in an area of the body, the tube distal end 142 is positioned in the area by inserting the distal end through a cannula or through an incision to position the tube distal end 148 at the surgical site. An instrument, for example a surgical grasper is then inserted through the tube 142 until it emerges from the tube distal end 148. The surgical grasper then grasps the second tissue connector 14 at the hook 72. The surgical grasper is then removed through the tube 142 moving the second connector 14 hook first into the tube distal end and pulling the cord into the tube distal end 142. The cord 16 is then continued to be pulled through the tube until the tapered configuration of the base proximal end surface 28 of the first tissue connector 12 is pulled into the tube distal end 148. The tapered configuration of the proximal end surface 28 centers the base cylindrical side surface 24 of the first tissue connector 12 relative the tube interior bore as the tapered proximal end surface is pulled into the tube interior bore. With the base cylindrical side surface 24 centered in the interior bore of the tube 142, the hook 22 projecting from the base distal end surface 30 is prevented from snagging or catching the distal end 148 of the tube 142 as the first tissue connector is pulled into and through the tube.

Thus, as described above, the apparatus of the invention and its method of use facilitate the delivery of surgical tissue connectors to a laparoscopic surgical site and facilitate the removal of the surgical connectors from the surgical site.

As various modifications could be made in the apparatus herein described and illustrated and its method of use without departing from the scope of the invention, it is intended that all the matter contained in the foregoing description or shown in the accompanying drawings shall be interpreted as illustrative rather than limiting. Thus, the breath and scope of the present invention should not be limited by any of the above described exemplary embodiments, but should be defined only in accordance with the following claims appended hereto and their equivalents.

We claim:

1. A method of retracting a first internal organ of a patient, said method comprising the steps of:
   providing a retractor system comprising:
   a first tissue connector (12) including a base (18) and a hook (22) secured to the base, the first tissue connector having a proximal end surface (28) and a distal end surface (30) at axially opposite ends of a base side surface (24); and
   a second tissue connector (14) comprising:
      an additional base (68) and an additional hook (72) secured to the additional base;
      an interior bore (102) and a pin (106) extending across the interior bore;
   a cord (16, 54, 56, 114, 112, 116) characterized by a cord first end (54) and a cord second end (56), and said cord second end characterized by a cord first portion (114), a cord second portion (116) and a cord intermediate portion (112), said cord first portion (116) connected to and extending from an additional base proximal end surface (78) toward the first tissue connector (12); and
   an actuator including a releasable one-way cord lock through which the cord second end (56, 114, 112, 116) passes, said releasable one-way cord lock comprising a lock pin (126) axially slidably disposed in a first axially extending slot (124) disposed in the additional base, said lock pin (126) extending across the interior bore of the additional base (68), and a sleeve (128) surrounding an additional base side surface (74) and axially slidable between first and second positions relative to the additional base (68), said sleeve (128) secured to the lock pin (126);
   inserting the first tissue connector (12) through a tube (142) and connecting it to a first location within the abdomen of the patient;
   inserting the second tissue connector (14) through the tubular delivery device and connecting it to a second location within the abdomen of the patient and extending the cord under the first internal organ; and
   adjusting a length of the cord second portion (116) extending from the second tissue connector (14) in order to decrease a length of the cord first portion extending toward the first tissue connector (12) to move the first internal organ to a position away from the second internal organ, and operating the actuator to lock the cord second end (56, 114, 112, 116) to the additional base (68).

2. The method of claim 1 further comprising:
   sliding the sleeve (128) to cause the lock pin (126) to engage against a cord intermediate portion (112) to prevent movement of the cord first end (54) away from the additional base proximal end surface (78) of the second tissue connector (14).

3. The method of claim 2 further comprising:
   moving the actuator (128) to the first position to cause the lock pin (126) to engage against the cord intermediate portion (112) that is wrapped around the rod (106).

4. The method of claim 3 further comprising: moving the actuator (128) to the second position to cause the lock pin (126) to disengage from the cord intermediate portion (112) and allow the length of the cord first portion extending between the second tissue connector (14) and the first tissue connector (12) to be pulled from the second tissue connector to adjust or increase the length of the cord first portion (114).

5. The method of claim 1 wherein:
   the second tissue connector (14) further comprises a biasing device (132) disposed within the bore (102) of the second tissue connector (14) and the method further comprises the step of:
   operating the biasing device to urge the lock pin (126) toward an intermediate position.

6. The method of claim 1 wherein:
   the second tissue connector (14) further comprises a side hole in the additional base side surface (74) and the cord second portion (116) passes through the side hole thereby separating the cord first portion (114) and the cord second portion (116) to prevent tangling of the cord, and
   the method further comprises the step of:
   pulling the cord second portion (116) through the side hole to accomplish the step of decreasing the length of the cord first portion (114) extending toward the first tissue connector.

7. The method of claim 1 wherein:
   the retractor system comprises a third tissue connector (136) connected to the second tissue connector through a second cord (134), and the method further comprises the step of: connecting the third tissue connector (136) to a third location within the abdomen of the patient.

8. The method of claim 1 further comprising:
   inserting a surgical grasper through the tube (142) and grasping the second tissue connector (14) at the additional hook (72) and moving the second tissue connector (14) hook-first into a tube distal end (148) and thereafter pulling the cord into the tube distal end and then continuing to pull the cord (16, 54, 56, 114, 112, 116) through the tube (142) until the base proximal end surface of the first tissue connector (12) is pulled into the tube distal end and removing the second tissue connector (14) and the first tissue connector (12) from the surgical site.

* * * * *